United States Patent
Dooney, Jr. et al.

(10) Patent No.: US 9,089,363 B2
(45) Date of Patent: Jul. 28, 2015

(54) ARTHROSCOPIC CANNULA DAMS FOR FLUID CONTROL

(71) Applicant: Arthrex, Inc., Naples, FL (US)

(72) Inventors: Thomas Dooney, Jr., Naples, FL (US); Derek C. Sullivan, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/057,395

(22) Filed: Oct. 18, 2013

(65) Prior Publication Data

US 2014/0121630 A1 May 1, 2014

Related U.S. Application Data

(60) Provisional application No. 61/719,037, filed on Oct. 26, 2012.

(51) Int. Cl.
*A61M 5/178* (2006.01)
*A61B 17/34* (2006.01)

(52) U.S. Cl.
CPC ......... *A61B 17/3423* (2013.01); *A61B 17/3421* (2013.01); *A61B 17/3498* (2013.01)

(58) Field of Classification Search
CPC .......... A61M 39/06; A61M 2039/064; A61M 2039/066; A61M 2039/0633; A61M 2039/0653; A61M 2039/0686; A61B 17/3498; A61B 17/3421
USPC ................ 604/158, 167.01–167.06, 256, 264
See application file for complete search history.

(56) References Cited

U.S. PATENT DOCUMENTS

| | | | |
|---|---|---|---|
| 5,009,391 A | | 4/1991 | Steigerwald |
| 5,180,365 A | * | 1/1993 | Ensminger et al. ...... 604/288.03 |
| 5,743,884 A | * | 4/1998 | Hasson et al. ........... 604/167.02 |
| 7,850,653 B2 | * | 12/2010 | Hammond ............... 604/167.02 |
| 2003/0195472 A1 | * | 10/2003 | Green et al. ............. 604/167.04 |
| 2005/0065535 A1 | * | 3/2005 | Morris et al. ................ 606/148 |
| 2009/0137943 A1 | | 5/2009 | Stearns et al. |
| 2010/0179479 A1 | * | 7/2010 | Albrecht et al. ......... 604/167.01 |
| 2010/0191261 A1 | * | 7/2010 | Carter et al. .................. 606/150 |
| 2010/0234688 A1 | * | 9/2010 | Carter .......................... 600/208 |
| 2010/0268162 A1 | * | 10/2010 | Shelton et al. ........... 604/167.01 |
| 2010/0274193 A1 | * | 10/2010 | Patton et al. ............. 604/167.01 |
| 2010/0298775 A1 | * | 11/2010 | Berry et al. .............. 604/167.03 |
| 2012/0041271 A1 | * | 2/2012 | Wenchell et al. ............. 600/208 |

(Continued)

FOREIGN PATENT DOCUMENTS

| | | |
|---|---|---|
| EP | 0 143 518 A1 | 6/1985 |
| EP | 1 127 550 A1 | 8/2001 |

(Continued)

*Primary Examiner* — Nicholas Lucchesi
*Assistant Examiner* — Gerald Landry, II
(74) *Attorney, Agent, or Firm* — Dickstein Shapiro LLP (57) ABSTRACT

A cannula with a tri-slot dam assembly including two primary dams as the main fluid seal and an adjacent outer "baffle-like dam" that prevents fluid pressure build-up and allows the fluid to leak out and not squirt out of the cannula. The baffle-like dam has a body formed of a low profile material and is provided with a plurality of small through holes or perforations to allow fluid to gently leak out. Fluid that enters the outer chamber leaks out of the through holes so that the fluid pressure between the baffle and the primary dams is very low. A spacer is optionally provided between the two primary dams and the outer dam to prevent the dams from interfering with each other and allow them to remain open.

16 Claims, 7 Drawing Sheets

(56) References Cited

U.S. PATENT DOCUMENTS

2012/0238827 A1* 9/2012 Berry et al. .................. 600/210
2013/0310751 A1* 11/2013 Davis et al. .............. 604/164.12

FOREIGN PATENT DOCUMENTS

| EP | 2 228 016 A1 | 9/2010 |
| WO | WO 2008/147931 A1 | 12/2008 |

* cited by examiner

Section A-A
FIG. 6(b)

ARTHROSCOPIC CANNULA DAMS FOR FLUID CONTROL

CROSS-REFERENCE TO RELATED APPLICATIONS

This application claims the benefit of U.S. Provisional Application No. 61/719,037, filed Oct. 26, 2012, the disclosure of which is incorporated by reference in its entirety herein.

FIELD OF THE INVENTION

The present invention relates to methods and apparatus for surgical procedures.

BACKGROUND OF THE INVENTION

Minimally invasive surgeries (such as endoscopic surgery) are performed via portals through which a variety of elongated instruments may be passed to gain access to an internal surgical site. Cannulas are often inserted into portals to provide a convenient passageway through which the various instruments may pass. When cannulas are inserted through portals formed in walls of the body, it is desirable that the cannulas be provided with means for controlling the release of fluid (for example, irrigation fluid) within the body.

Because many arthroscopic procedures require the use of pressurized fluid to distend and irrigate the joint being operated upon, the cannula must provide a sealed passageway to enable instruments to be passed into and out of the cannula while maintaining a fluid seal to prevent squirting whether or not an instrument is in the cannula passageway. The sealing of such cannula passageways is usually accomplished by one or more membranes (dams) attached to the proximal end of the elongated cannula. Current arthroscopic cannulas experience fluid leakage when an instrument is placed through the membranes (dams) of the cannula. When the dams are broken, the pressure release allows the fluid to squirt out of the cannula and disrupt the surgery.

There is a need for a cannula that is used in minimally invasive procedures and that has increasing fluid sealing capabilities to prevent fluid from squirting from within the body when instruments are passing through the cannula. A cannula that allows the fluid to gently leak out (and not squirt) is also needed.

SUMMARY OF THE INVENTION

The present invention provides a tri-slot dam cannula comprising two primary dams as the main fluid seal and an adjacent outer "baffle-like dam" that prevents fluid pressure build-up and allows the fluid to leak out and not squirt out of the cannula. The baffle-like dam has a body formed of a low profile material and is provided with a plurality of through holes to allow fluid to gently leak out. Fluid that enters the outer chamber leaks out of the through holes so that the fluid pressure between the baffle and the primary dams is very low.

The present invention also provides methods of conducting surgery by: (i) providing a cannula that includes primary dams (main fluid seals) adjacent an outer "baffle-like dam" with a plurality of through holes to prevent fluid pressure build-up; and (ii) controlling fluid flow by allowing fluid under pressure to leak out of the through holes of the "baffle-like dam" (and not squirt out of the cannula) during a surgical procedure.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 6(*a*) is a perspective view of the dam/baffle with holes (the third seal) of the cannula of FIG. 3.

FIG. 6(*b*) is a side view of the dam/baffle with holes (the third seal) of FIG. 6(*a*).

FIG. 6(*c*) is a front view of the dam/baffle with holes (the third seal) of FIG. 6(*a*).

FIG. 6(*d*) is an enlarged view of the center portion of the dam/baffle with holes (the third seal) of FIG. 6(*a*).

FIG. 7(*a*) illustrates a perspective view of the backup seal (the second seal) of the cannula of FIG. 3.

FIG. 7(*b*) is a front view of the backup seal (the second seal) of FIG. 7(*a*).

FIG. 7(*c*) is a side view of the backup seal (the second seal) of FIG. 7(*a*).

FIG. 8(*a*) illustrates a perspective view of the cross-slit dam (the first seal) of the cannula of FIG. 3.

FIG. 8(*b*) is a front view of the cross-slit dam (the first seal) of FIG. 8(*a*).

FIG. 8(*c*) is a side view of the cross-slit dam (the first seal) of FIG. 8(*a*).

FIG. 9(*a*) illustrates a cannula assembly of the present invention with an obturator and an exploded view of another exemplary embodiment of a cannula of the present invention (with an additional spacer component).

FIGS. 9(*b*) and 9(*c*) illustrate the cannula assembly of FIG. 9(*a*) in the assembled state (final assembly shown in FIG. 9(*c*)).

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a cannula with two primary dams as the main fluid seal and with an additional adjacent outer "baffle-like dam" that prevents fluid pressure build-up and allows the fluid to leak out and not squirt out of the cannula. The baffle has a body formed of a low profile material with through-holes (perforations) to allow fluid to gently leak out of the cannula. Fluid that enters the outer chamber leaks out of the holes so that the fluid pressure between the baffle and the primary dams is very low.

The present invention also provides a cannula assembly comprising a main cannula and a baffle-like dam adjacent the main cannula. The baffle-like dam may be attached to or integral with the main cannula. The baffle-like dam may be removable from the main cannula. The baffle-like dam may be also designed to be retrofitted on existing cannulas. The baffle-like dam controls fluid flow by allowing fluid under pressure to gently leak out of the main cannula.

The present invention also provides methods of conducting surgery by inter alia: (i) providing a cannula comprising a primary seal (dam) and a dam/baffle adjacent the primary seal; and (ii) controlling fluid flow by allowing fluid to leak out of the cannula, through a plurality of through holes (perforations) in the dam/baffle, during a surgical procedure.

Figure 1:
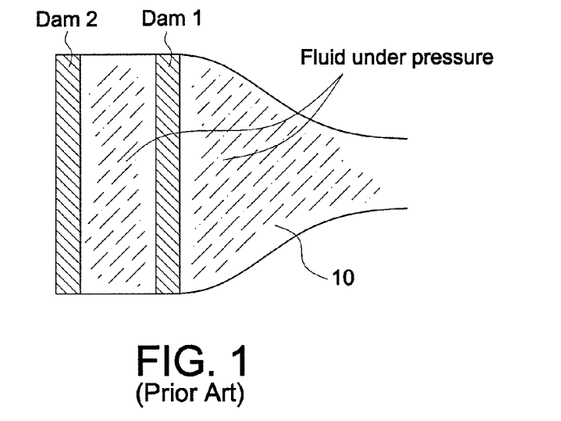
FIG. 1 shows a prior art cannula.
Figure 2:
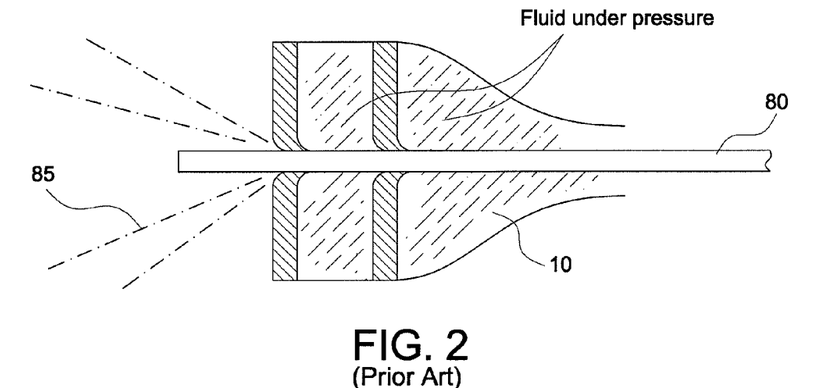
FIG. 2 shows how fluid squirts out of the cannula of FIG. 1 due to the high pressure of the fluid.
Figure 3:
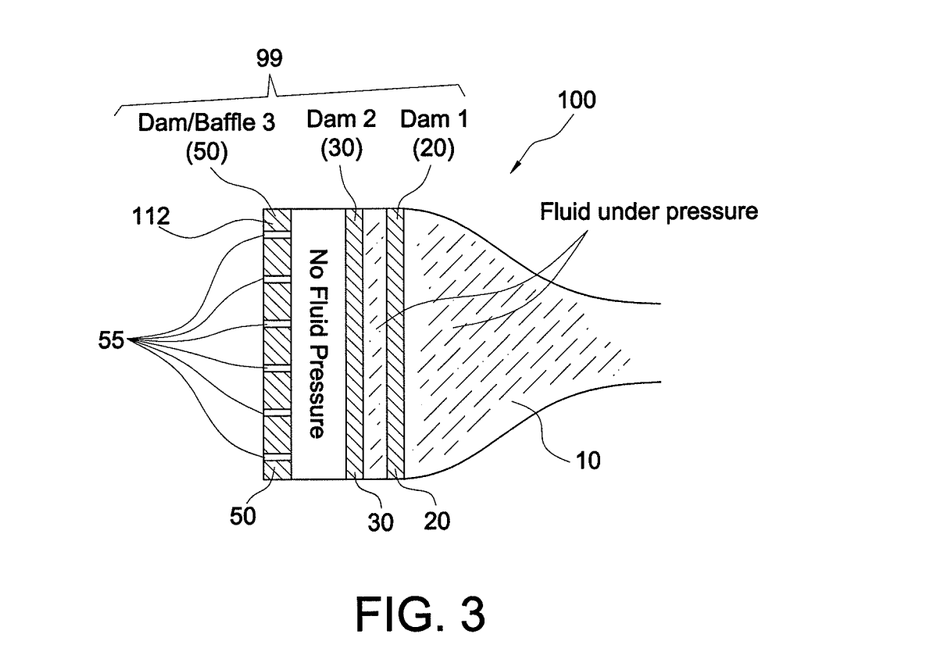
FIG. 3 illustrates an exemplary embodiment of a cannula of the present invention comprising a cross-slit dam (a first seal), a backup seal (a second seal) and a dam/baffle with through holes (a third seal).

Referring now to the drawings, where like elements are designated by like reference numerals, FIGS. 1 and 2 illustrate an exemplary embodiment of a prior art cannula 10, while FIGS. 3-8 illustrate various views of an exemplary embodiment of a cannula 100 of the present invention (and its components).

Prior art cannula 10 of FIG. 1 includes two dams or fluid seals, Dam 1 and Dam 2, provided within the body of cannula 10. As shown in FIG. 2, when instrument 80 is inserted into cannula 10, fluid 85 undesirably squirts out of the cannula due to the high pressure build-up which takes place between Dam 1 and Dam 2.

FIGS. 3-8(c) illustrate various views and components of an exemplary cannula 100 of the present invention. As shown more clearly in FIGS. 3-5, cannula 100 includes an improved sealing system 99 (a tri-slot dam assembly 99) provided by two dams or seals 20, 30 (a first fluid seal 20 and a second fluid seal 30) and with an outer baffle-like dam 50 (a third fluid seal 50 or baffle 50) adjacent the two dams or seals.

Figure 5:
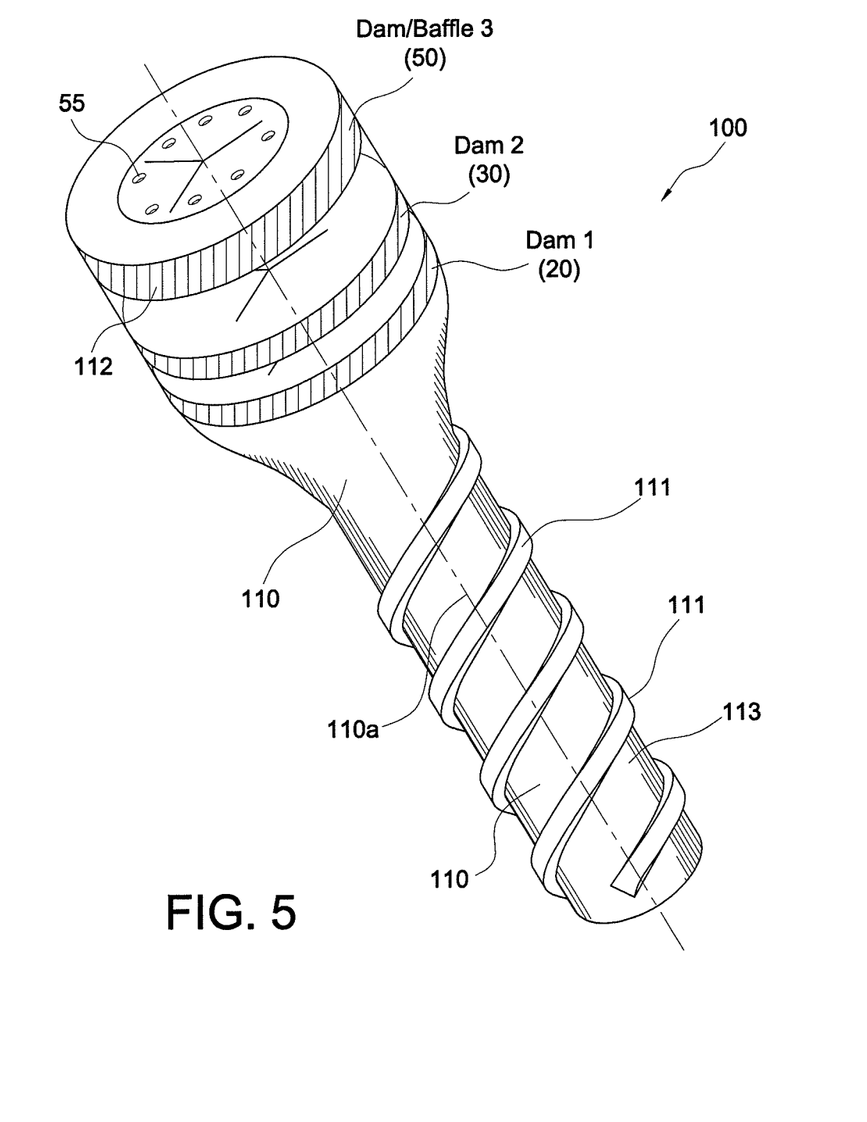
FIG. 5 is a perspective view of the cannula of FIG. 3.
Figure 6A:
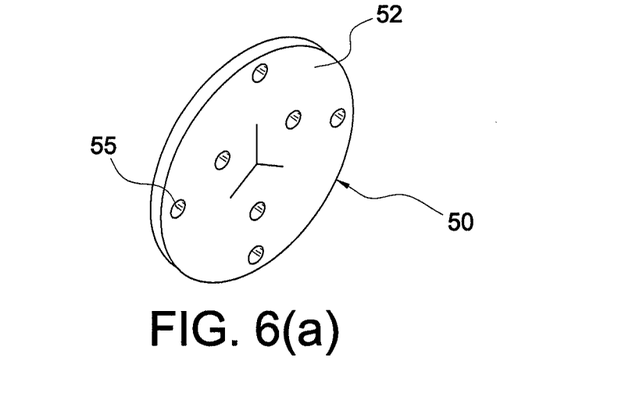
Figure 6B:
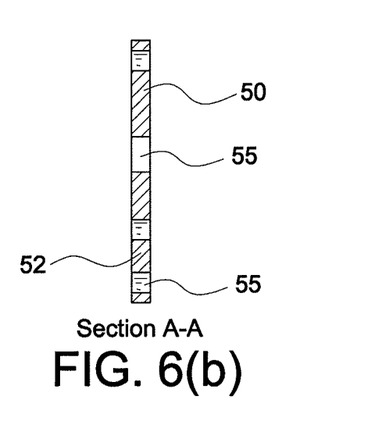
Figure 6C:
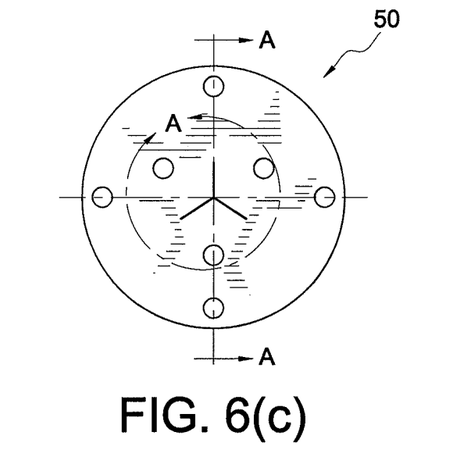
Figure 6D:
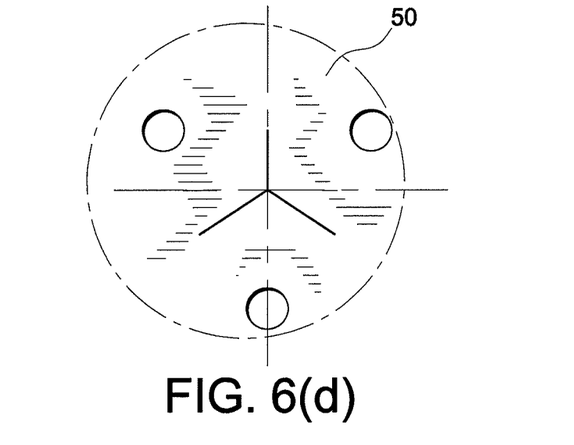
Figure 7A:
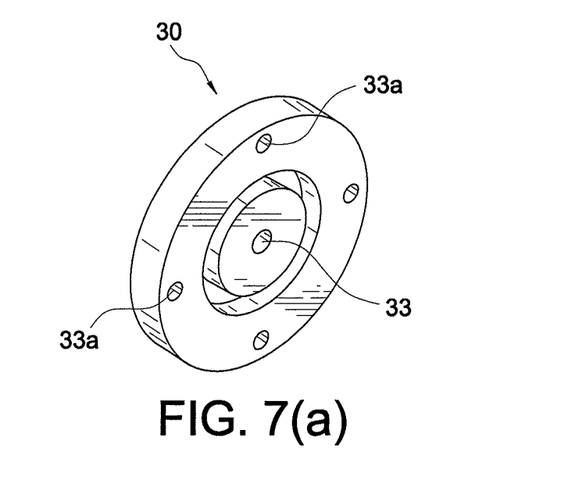
Figure 7B:
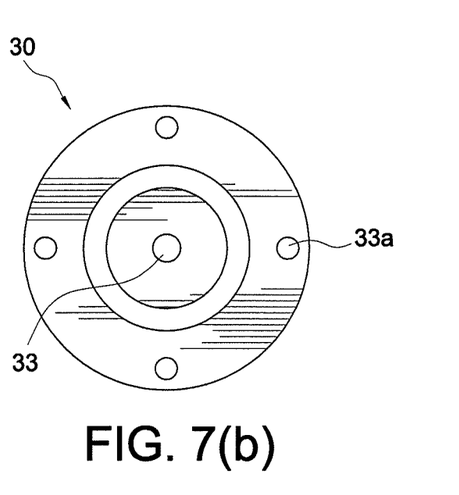
Figure 7C:
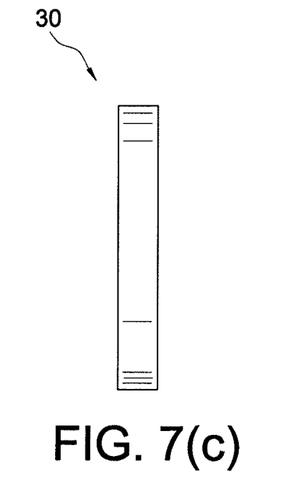

As schematically illustrated in FIG. 5, cannula 100 comprises an elongated body 110 having a longitudinal axis 110a, a distal end 113 and a proximal end 112. The elongated body 110 of cannula 100 may be flexible or rigid, may be slidably movable relative to a cylindrical sleeve, and may be provided with a plurality of threads 111, as shown in FIG. 5. Threads 111 may be provided on the whole length of the elongated body 110 (as shown in FIG. 5) or, alternatively, on at least a length of the body 110, or the cannula may have no threads at all on the body.

An outflow/inflow port (not shown) is provided at the proximal end 112 of the body 110 of cannula 100. The outflow/inflow port may be a fluid passage with various configurations and cross-sections, for example, a tubular configuration. The outflow/inflow port may be connected to a source of fluid or irrigation solution, gas, or vacuum, for supplying irrigation or gas through the cannula to the work site during the arthroscopic procedure.

The tri-slot dam assembly 99 includes a first fluid seal or dam 20, a second fluid seal or dam 30 and an outer fluid seal or dam 50. The tri-slot dam assembly 99 is oriented in a direction about perpendicular to the longitudinal axis 110a of the elongated body 110.

Figure 8A:
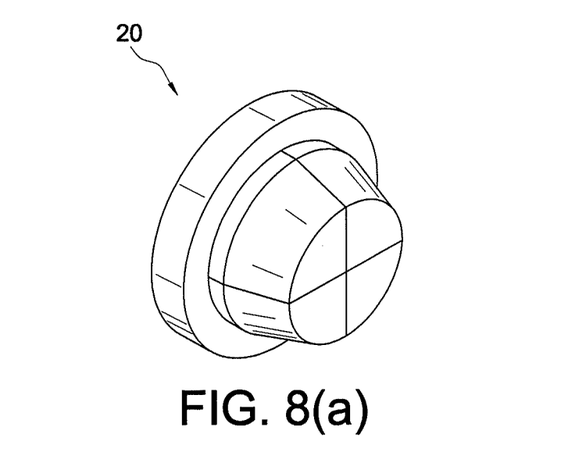
Figure 8B:
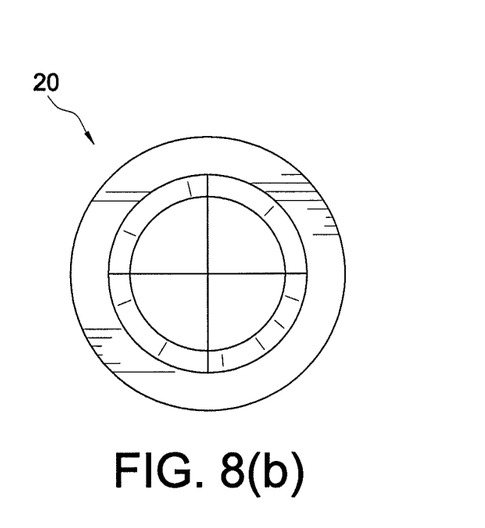
Figure 8C:
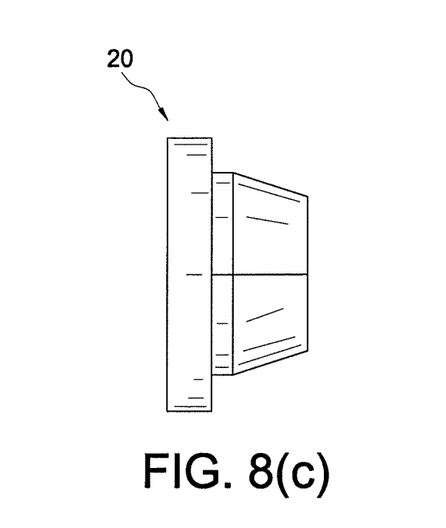

First fluid seal or dam 20 of the tri-slot dam assembly 99 is shown in more details in FIGS. 8(a)-8(c) and may be an exemplary cross-slit dam in the form of a flexible membrane of an exemplary 8.25" twist in cannula. Second fluid seal or dam 30 of the tri-slot dam assembly 99 is shown in more details in FIGS. 7(a)-7(c) and may be a backup seal in the form of a flexible membrane of an exemplary 8.25" twist in cannula provided with at least one through hole 33 or a slit large enough for surgical instrumentation. Holes 33a provided on the perimeter of the second fluid seal 30 are for cannula assembly only and they snap together with the other cannula components. First and second fluid seals or dams 20, 30 form a primary fluid seal.

Figure 4:
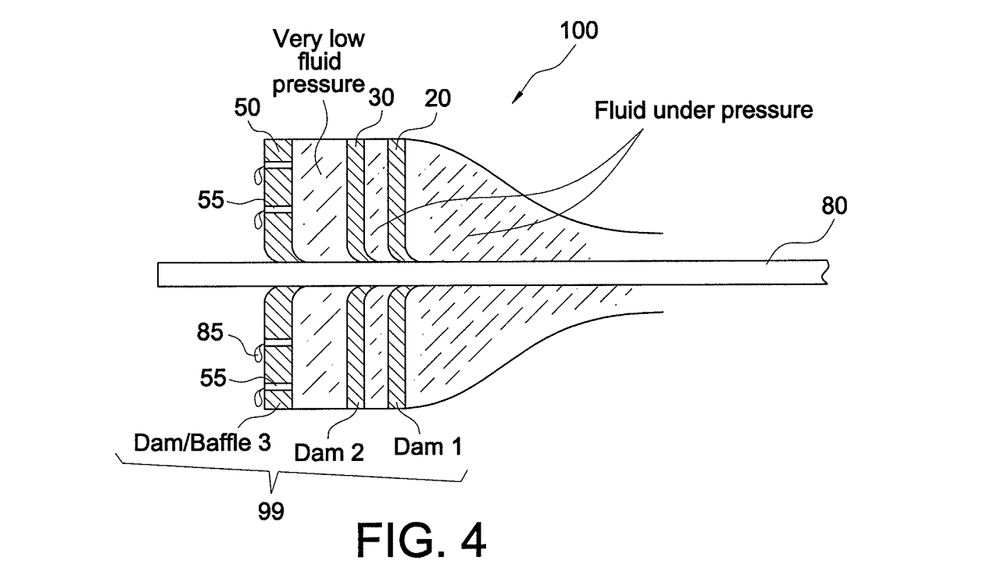
FIG. 4 shows how fluid leaks out (and without squirting) of the cannula of FIG. 3.

The baffle-like dam 50 (the third fluid seal 50) of the tri-slot dam assembly 99 is shown in more details in FIGS. 6(a)-6(d) and may be part of an exemplary 8.25" twist in cannula. The baffle-like dam 50 is also in the form of a flexible membrane with a plurality of through holes or perforations 55 with a diameter small enough to permit fluid 85 to gently leak out of the cannula. Through holes 55 prevent fluid build-up and thus prevent fluid from squirting under pressure out of the cannula 100 (as shown in FIG. 4).

Baffle-like dam 50 (third fluid seal 50) may be provided integral with the other cannula components, for example, integral with the first and second fluid seals 20, 30. Baffle-like dam 50 (third fluid seal 50) may be also designed to be retrofitted on an existing cannula (which is already provided with a sealing mechanism such as the one shown in FIGS. 1 and 2, or with a different sealing mechanism). Baffle-like dam 50 has a body 52 formed of a low profile material with holes 55 that allow fluid 85 to gently leak out of the cannula. Fluid leaks out of the holes 55 so that the fluid pressure between the baffle and the primary dams 20, 30 remains low.

At least one of fluid seals 20, 30, 50 may be formed of silicon or a similar material. Alternatively, all three seals could be formed of silicon or a similar material.

Figures 9A, 9B, 9C:
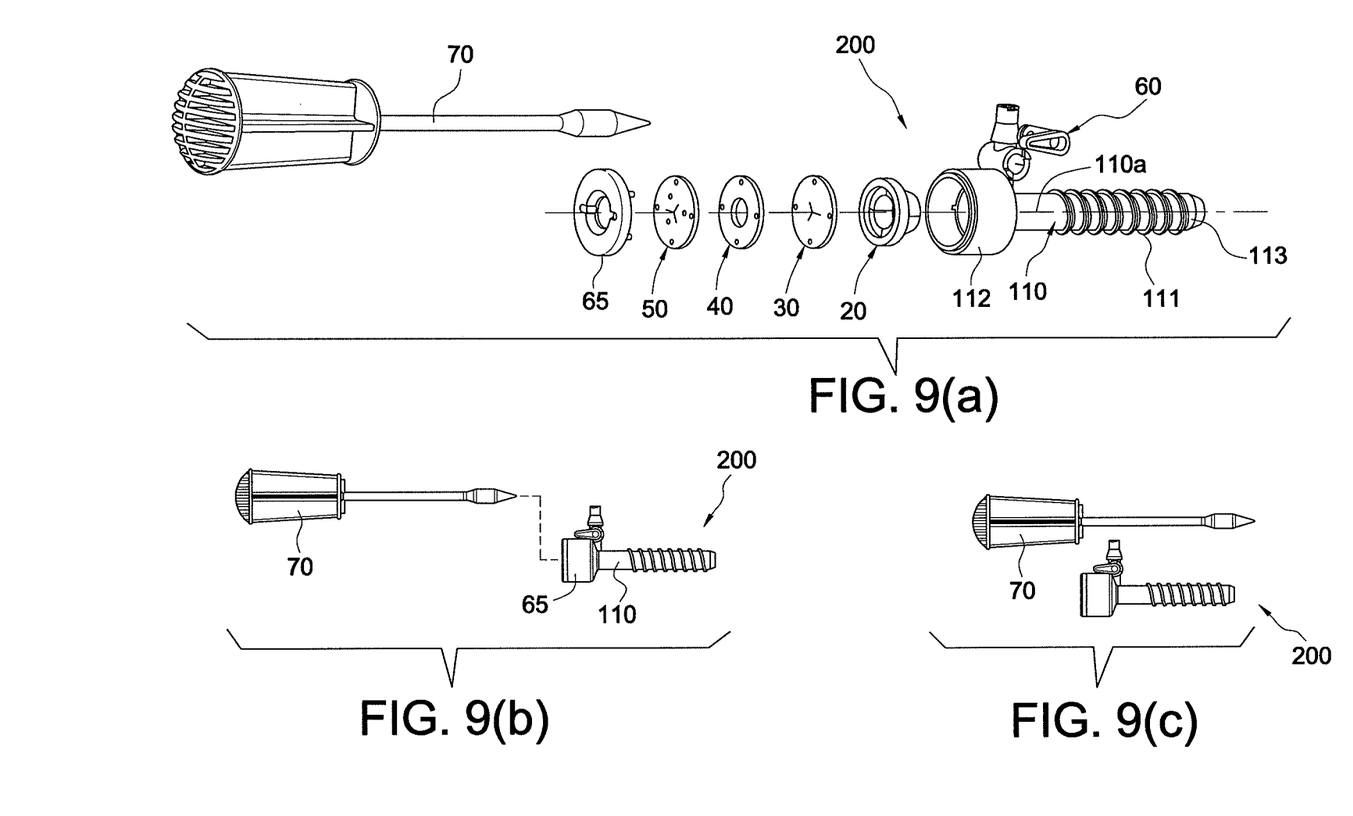

FIGS. 9(a)-9(c) illustrate another embodiment of an exemplary 8.25" twist in cannula assembly comprising an obturator 70 and cannula 200 according to yet another exemplary embodiment of the present invention. Cannula 200 of FIGS. 9(a)-9(c) is similar in part with cannula 100 detailed above but differs in that cannula 200 is provided with an additional spacer component added between the inner and outer tri-slot dams (i.e., between the outer fluid seal and the primary fluid seal). The addition of another spacer component aids to prevent the tri-slot dams from interfering with each other and remaining open.

FIG. 9(a) shows an exploded view of the elements of exemplary cannula 200. Cannula 200 may be an exemplary 8.25" twist in cannula. The dams are inserted in the order shown in FIG. 9(a). Cannula 200 includes body 110, cap 65, valve 60 (inflow/outflow port 60), outer tri-slot dam 50, spacer 40, inner tri-slot dam 30, and cross-slit dam 20. Cap 65 may be attached by any known method in the art, for example, by welding such as ultrasonic welding. Valve 60 is inserted in the orientation shown to securely snap into body 110. The tri slots for the outer and inner tri-slot dams 50, 30 are about 90 degrees offset, as shown in FIG. 9(a). FIGS. 9(b) and 9(c) show the final assembly of cannula 200 with exemplary obturator 70.

Although the cannula 100, 200 of the invention can readily be used in large body cavities such as the abdomen, it is particularly useful in smaller cavities such as joints (i.e., knees, shoulders, elbows, ankles, and the like). During arthroscopic surgery of a joint, the joint is typically inflated with water as opposed to a gas, which is typically used in abdominal surgical procedures, as the surgical procedures performed within a joint are significantly different from those performed within an abdominal cavity. Employing cannula 100, 200 of the present invention in arthroscopic surgeries of joints provides a low-cost, simple method for controlling the release of fluid (for example, water or irrigation fluid) within the joint cavity.

An exemplary method of conducting surgery comprises inter alia the steps of: (i) providing a cannula 100, 200 comprising a primary seal (dam) 20, 30 and an outer fluid dam/baffle 50 adjacent the primary seal 20, 30, and optionally a spacer 40 provided between the outer dam/baffle 50 and the primary seal (dam) 20, 30; and (ii) controlling fluid flow by allowing fluid to leak out of the cannula 100, 200 through a plurality of small through holes 55 (perforations 55) provided in the body 52 of the dam/baffle 50, during a surgical procedure.

Cannula 100, 200 of the present invention may be formed as a single piece, clear cannula and may be preferably formed of an elastomeric, tissue-compatible material such as silicone, for example, or combination of elastomeric or similar materials (with additional colorants, if desired).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A cannula for enabling passage of surgical instruments in the body, comprising:
    an elongated body having a proximal end, a distal end, and a longitudinal axis; and
    a tri-slot dam assembly disposed within the elongated body and at the proximal end, the tri-slot dam assembly comprising a first fluid seal and an adjacent second fluid seal, and an outer fluid seal having a baffle-like configuration, wherein the first fluid seal and the second fluid seal are integral with the proximal end, wherein the outer fluid seal is removably attached to and detached from the proximal end, and wherein the second fluid seal is provided with at least one through hole or slit to permit passage of one or more surgical instruments and with a plurality of holes provided on a perimeter of the second fluid seal for cannula assembly.

2. The cannula of claim 1, wherein the tri-slot dam assembly further comprises a spacer provided between the second fluid seal and the outer fluid seal.

3. The cannula of claim 1, wherein the outer fluid seal has a body provided with a plurality of through holes or perforations to allow fluid to gently leak and not squirt out of the elongated body.

4. The cannula of claim 1, wherein each of the first fluid seal, the second fluid seal and the outer fluid seal has a circular configuration with an outer diameter which is about equal to an inner diameter of the proximal end of the elongated body.

5. The cannula of claim 1, wherein the first fluid seal is a cross-slit dam.

6. The cannula of claim 1, wherein the tri-slot dam assembly prevents fluid from squirting out of the body when surgical instruments are being inserted through the cannula.

7. The cannula of claim 1, wherein the tri-slot dam assembly is oriented in a direction about perpendicular to the longitudinal axis of the body.

8. The cannula of claim 1, wherein at least one of the elongated body and the tri-slot dam assembly are formed of an elastomeric material.

9. The cannula of claim 1, further comprising a cap attached to the proximal end.

10. A cannula assembly comprising:
    a cannula comprising an elongated body with a plurality of threads, a proximal end, a distal end, a longitudinal axis, and a primary fluid seal disposed therein and integral with the proximal end, wherein the primary fluid seal comprises a first fluid seal and an adjacent second fluid seal, the first fluid seal and the second fluid seal being integral with the proximal end, and wherein the second fluid seal is provided with at least one through hole or slit to permit passage of one or more surgical instruments and with a plurality of holes provided on a perimeter of the second fluid seal for cannula assembly;
    an outer fluid seal or dam attached to the cannula adjacent the outer fluid seal, the outer fluid seal or dam comprising a flexible membrane with a plurality of through holes or perforations to allow fluid to gently leak and not squirt out of the elongated body; and
    a spacer provided between the primary fluid seal and the outer fluid seal.

11. The cannula assembly of claim 10, wherein the outer fluid seal or dam is positioned about perpendicularly to the longitudinal axis of the elongated body.

12. The cannula assembly of claim 10, wherein the outer fluid seal or dam is designed to be retrofitted on the cannula.

13. The cannula assembly of claim 10, wherein the outer fluid seal or dam is designed to be removably attached to and detached from the proximal end of the cannula.

14. A method of preventing extravasation when introducing a surgical instrument at an operative site through a portal in an endoscopic procedure, the method comprising:
    forming a portal through a wall of the body adjacent the operative site;
    positioning a cannula through the portal, the cannula comprising an elongated body having a plurality of threads, a proximal end, a distal end to be inserted through the portal, and a longitudinal axis; a primary fluid seal disposed within the elongated body and integral with the proximal end, wherein the primary fluid seal comprises a first fluid dam and an adjacent second fluid dam, the first fluid dam and the second fluid dam being integral with the proximal end, and wherein the second fluid dam is provided with at least one through hole or slit to permit passage of one or more surgical instruments and with a plurality of holes provided on a perimeter of the second fluid dam for cannula assembly; and an outer fluid seal or dam provided within the elongated body and adjacent the primary fluid seal at the proximal end, wherein the outer fluid seal or dam is provided with a plurality of through holes or perforations to allow fluid to leak out while preventing fluid from squirting out of the body when a surgical instrument is being inserted through the cannula, and while preventing fluid pressure within the primary fluid seal; and
    introducing the surgical instrument through the elongated body of the cannula.

15. The method of claim 14, wherein the cannula further comprises a spacer located between the primary fluid seal and the outer fluid seal or dam.

16. The method of claim 14, wherein each of the first and second fluid dams being is provided within a flexible membrane that prevents fluid from squirting from within the body during insertion of the cannula itself through the portal.

* * * * *